United States Patent [19]

Needham

[11] 3,995,625
[45] Dec. 7, 1976

[54] INHALATION DEVICES

[75] Inventor: David Alan Needham, Keighley, England

[73] Assignee: Cyprane Limited, Keighley, England

[22] Filed: Oct. 15, 1974

[21] Appl. No.: 514,763

[30] Foreign Application Priority Data

Oct. 18, 1973 United Kingdom ............. 48648/73

[52] U.S. Cl. .......................... 128/142.2; 128/210; 128/145.8
[51] Int. Cl.² ........................................ A61M 16/00
[58] Field of Search ...................... 128/145.5–145.8, 128/142–142.3, 146.4, 146.5, 184, 203, 209, 210, 196, 197, 277; 137/DIG. 9

[56] References Cited

UNITED STATES PATENTS

| | | | |
|---|---|---|---|
| 2,483,698 | 10/1949 | Goodner | 128/145.8 |
| 2,897,833 | 8/1959 | Seeler | 137/DIG. 9 |
| 2,908,270 | 10/1959 | Stanton | 128/145.8 |
| 3,083,707 | 4/1963 | Seeler | 128/145.8 |
| 3,726,274 | 4/1973 | Bird et al. | 128/145.8 |
| 3,850,171 | 11/1974 | Ball et al. | 128/145.8 |
| 3,853,105 | 12/1974 | Kenagy | 128/145.8 |
| 3,866,622 | 2/1975 | Kasahara et al. | 128/145.8 |

FOREIGN PATENTS OR APPLICATIONS

1,124,606  8/1968  United Kingdom

*Primary Examiner*—Robert W. Michell
*Assistant Examiner*—Henry J. Recla
*Attorney, Agent, or Firm*—Jay L. Chaskin

[57] ABSTRACT

A device for providing a gas-air mixture to a patient in response to suction applied by the patient, comprising means defining an air inlet, a backward-facing step, an air passage for directing air past said backward-facing step, a non-return valve for controlling flow of air from said inlet to said air passage and a gas passage communicating with said air passage through at least one orifice adjacent to said backward-facing step.

5 Claims, 2 Drawing Figures

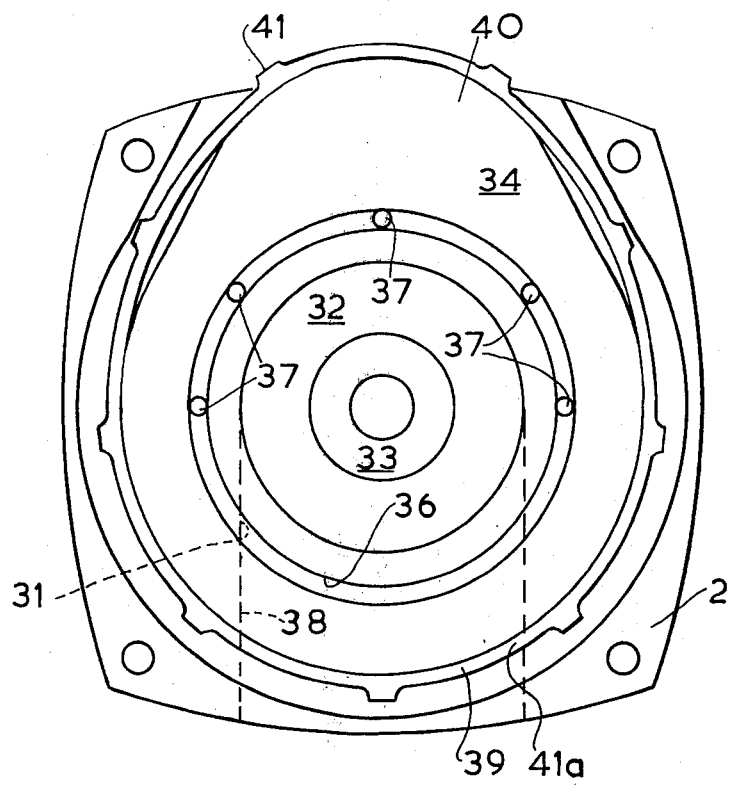
-FIG.2-

INHALATION DEVICES

This invention relates to devices for use in inhalation therapy and patient administered analgesia. Devices are known which respond to suction by a patient to open a demand valve allowing inhalation of oxygen or a mixture of gases by the patient.

In the field of inhalation therapy the patient may often be seriously ill, so that despite the self-administered oxygen there is a risk that breathing may stop. Emergency resuscitation of such patients calls fo an immediate supply of substantially pure oxygen at a pressure high enough to inflate the patient's lungs, which may then be deflated by pressure on the chest, these actions being repeated rhythmically until normal breathing recommences. To allow intermittent positive pressure ventilation of the patient's lungs known oxygen demand valves have incorporated a manually operated valve which allows the nursing staff to override the demand made of operation.

When a demand valve is used to supply oxygen in response to patient suction for the purpose of inhalation therapy or in conjunction with a draw-over anaesthetic vaporizer for the purpose of self-administered analgesia it may be desirable to dilute the flow of oxygen provided by the demand valve with air taken from the atmosphere. It is further desirable to be able to adjust the said dilution in order to administer to the patient a known concentration of oxygen in the oxygen enriched air. It is further desirable that the provision for dilution of the oxygen with air should not interfere with the facility to administer pure oxygen for resuscitation by manually overriding the demand valve.

Known devices which are employed to dilute a gas with atmospheric air usually make use of convergent-divergent passage or venturi through which one or other of the gases is drawn by the patients suction effort and in the narrowest section or throat of said passage, where the pressure is sub-atmospheric, the other gas is entrained. The entrained gas may enter via transverse ports in the venturi or through a co-axial pipe facing downstream. This arrangement has the disadvantage that on emergency resuscitation a relatively high pressure flow of pure oxygen through such a venturi will entrain a certain amount of air, unless positive steps are taken to close off the air supply. This results in a possibly substantial dilution of the oxygen received by the patient at a critical time when the purity of the oxygen is most important.

The known devices also suffer from the disadvantage that the percentage of oxygen in the diluted flow varies substantially with the suction effort applied by the patient. Particularly if the patient is breathing in a very shallow manner the oxygen percentage may become dangerously low.

According to the present invention a device for providing a gas-air mixture to a patient in response to suction applied by the patient comprises means defining an air inlet, a non-return valve for controlling flow of air from the inlet to an air passage for directing incoming air past a backward-facing step, and a gas passage communicating with the air passage through at least one orifice adjacent to the backward-facing step.

In normal patient demand use the act of sucking in the device will cause air to flow through the non-return valve and passage and past the backward-facing step. The lower pressure created by the air flow in the region of this step will cause the gas to flow through the orifice and mix with the air. The gas will usually be oxygen, but it may be nitrous oxide or another analgesic gas or vapor, or a mixture of oxygen with an analgesic gas or vapour.

The supply of gas will generally be obtained from a demand valve, and therefore a finite pressure drop must be achieved at the backward-facing step in order to overcome the triggering pressure necessary to cause the demand valve to operate and allow gas to pass. Provision of the non-return valve in the air inlet assists in creating this pressure drop. The valve is chosen to have opening characteristics related to the triggering characteristics of the demand valve, and together with proper selection of the total cross-sectional area of the orifice or orifices ensures similar resistance to both air and gas flow and thus maintains a substantially constant mixture delivered to the patient over a wide range of breathing flow rates.

The non-return valve is the air inlet ensures that when the device is used for resuscitation of a patient by operation of a manual override valve which is preferably incorporated in the device, the high flow of gas through the orifice in the backward-facing step entrains little or no air.

In order to inflate a patient's lungs during resuscitation it is necessary to apply a positive pressure up to a maximum set by a pressure limiting valve which may either be incorporated in the demand valve or elsewhere in the breathing circuit. Thus, an additional function of the non-return valve in the air inlet port is to prevent escape of gas as the lung pressure increases during resuscitation, so enabling the desired inflation pressure to be reached. The non-return valve may be conveniently in the form of a flap valve (desirably of silicone rubber) covering an air inlet port and liftable from the port by patient applied suction.

Preferably the air inlet port is of annular form defined between radially inner and radially outer sections of material, and the backward-facing step is formed by providing a groove in the downstream face of the radially outer section of material, the orifice or orifices opening into the base of the groove.

The amount of air entering the port may be controlled in any one of a number of ways, and control of the air will of course result in control of the concentration of oxygen delivered to the patient.

An oxygen supply system incorporating a device according to the invention will now be described in more detail, by way of example only, with reference to the accompanying drawings in which:

FIG. 2 is a cross-section on the line II—II of FIG. 1, with a part removed.

Figure 1:
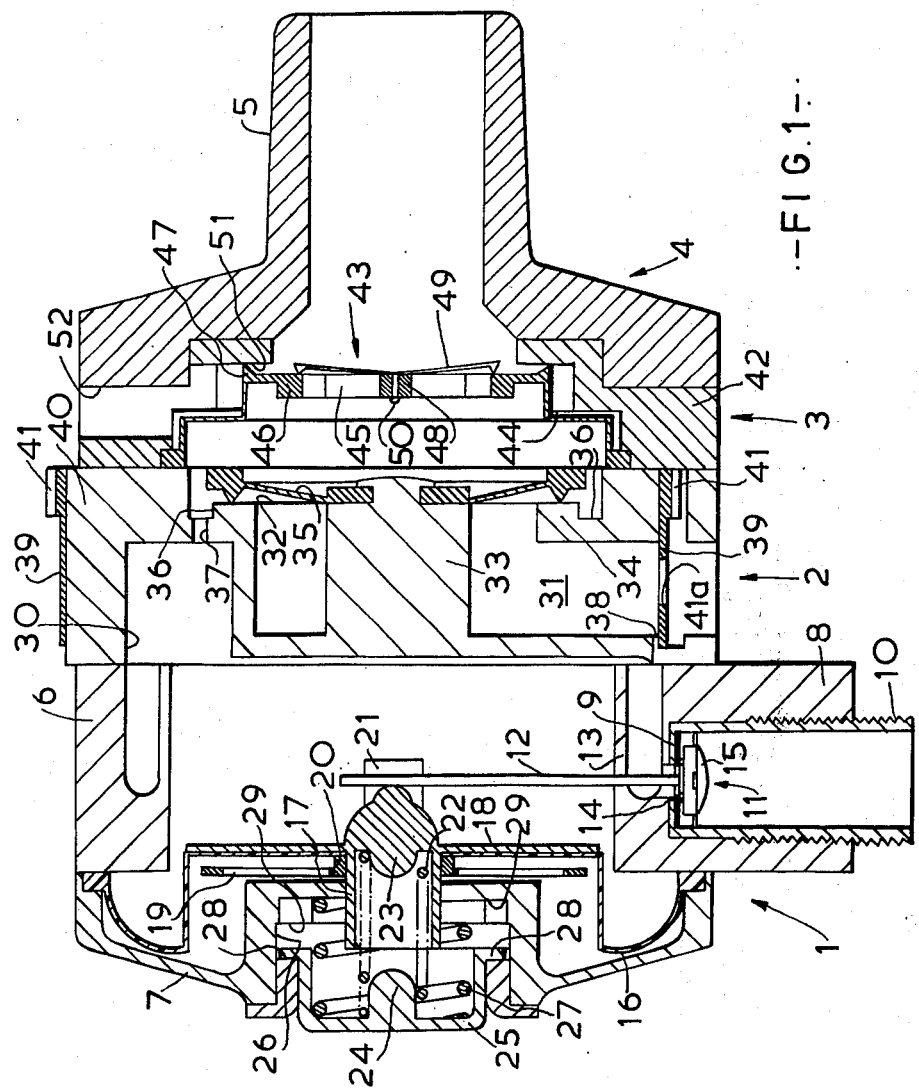
FIG. 1 is a longitudinal cross-section through the system.

The system shown comprises four modules which may be held together by bolts passing through all the modules. The modules comprise an oxygen demand valve module 1, a module 2 incorporating a device according to the invention, a no-rebreathing valve module 3 and an outlet module 4. The outlet module 4 has a stem 5 which the patient may place directly in his mouth, or which may be connected directly to a face mask or hose, or which may be plugged into the inlet to a draw-over anaesthetic vaporizer.

The oxygen demand valve module comprise a housing made up of sections 6 and 7, forming a first chamber, section 6 of which is formed with an oxygen inlet 8 in the base of which is a resilient valve seating 9. The inlet 8 has a coupling member 10 provided with a screw thread cut according to a system ensuring that only a particular nut will engage the thread. Seated in the inlet 8 is a valve member 11 having a stem 12 guided in a groove between two fingers, one of which is shown at 13. The valve member has a central sealing section 14 and an enlarged head 15.

Fitted between the sections 6 and 7 is the outer edge of a resilient diaphragm 16. A sleeve 17 passes through a central hole in the diaphragm and carries a radially extending web 18 lying against one side of the diaphragm. A further web 19 lies to the other side of the diaphragm and is secured to the sleeve by a boss 20. The diaphragm, sleeve and webs move together as a unit and the webs prevent the diaphragm from collapsing in either direction. One end of the sleeve 17 has two parallel extensions such as 21 between which the end of valve stem is located. A compression spring 22 is fitted over a pip 23 at the closed end of sleeve 17 and extends along the sleeve to fit at its other end over a pip 24 on an inflation oxygen supply button 25. This button is slidable in a recess 26 in the housing section 7 and is biased to a normal position as shown by a spring 27. The button has two diametrically opposed lugs 28 which may contact raised sections 29 in the base of recess 26. Alternatively, by rotating the button the lugs may be brought into register with spaces between raised sections 29.

The module 2 has a part-annular groove 30 in the upstream part thereof, which is in communication with the oxygen space in the body of section 7. An air inlet second chamber 31 is formed in the module 2 and communicates with an annular valve port 32 defined between radially inner and radially outer sections 33, 34 of the material forming the module. A diaphragm-type non-return valve 35 is secured to the downstream face of radially inner section 33 and can seal against the downstream face of radially outer section 34. This face is formed with a groove 36, and a number of orifices 37 open into the base of this groove and connect the groove 36 with the groove 30. The presence of the groove 36 results in a backward-facing step in the air passage where the air flows past the valve 35. For clarity the valve 35 is not shown in FIG. 2.

The air inlet chamber 31 has an intake opening 38 which may be sealed by a resilient band 39 passing around the periphery of the part defining the chamber. This part has a bulged section 40 causing the band to run in a substantially elliptical path and to be spaced from the part to either side of section 40. The outer face of the band has transverse ridges 41 which may be engaged to rotate the band, and the band is formed with a series of orifices 41a of different sizes, any required one of which may be brought into register with opening 38 by rotation of the band.

The third module 3 forming a third chamber has a housing 42 in which is mounted a diaphragm assembly 43, the circumferential edge of the assembly being located between housing 42 and the module 2. The assembly 43 has a flexible section 44 joining the edge to a web section 45 having a radially outer part 46 and a radially inner part 48 joined by radial members to the radially outer part. A flexible diaphragm 49 is fitted to the inner part 48 by a snapfit stud 50, and the diaphragm 49 seats on radially outer part 46. The outer part 46 has a sealing section 47 which may seat on a valve seating 51 formed on part of the housing 42. A passage 52 leading to atmosphere is formed in housing 42.

When used in the normal demand mode the operation is as follows. When suction is applied by the patient the diaphragm 49 lifts from seating 46 and the sealing section 47 of the diaphragm assembly seats on seating 51. The suction effect lifts diaphragm 35 from its seating and draws air past the diaphragm from chamber 31, the volume of air being regulated by the size of the orifice 41a which is positioned over the intake opening 38. The air flowing past diaphragm 35 also passes the groove 36 forming the backward-facing step and this movement creates a pressure reduction at the groove. The effect of this reduction and of the patient-applied suction acts to distort the diaphragm 16 to the right as seen in FIG. 1, so rocking the valve 11 initially about the edge of the sealing section 14 and then about the edge of the enlarged head 15. This allows oxygen under pressure to flow into the space in the body of section 7, into the groove 30 from where it is sucked through the passage 37 to be admixed with the air. The air/oxygen mixture is thus inhaled by the patient. On exhalation the diaphragm 49 seals on part 46 and flexible part 44 flexes so that sealing section 47 lifts off seating 51 opening a path to atmosphere through passage 52.

If emergency inflation of the patient is required then the button 25 is pressed to pivot valve 11 and allow an oxygen flow as already described. As there is no suction from the patient the diaphragm 35 does not lift so that no air is admitted into the system and the patient receives pure oxygen. The provision of the lugs 28 on button 25 and raised sections 29 and spaces in recess 26 allow a selection of the degree of opening of valve 11. When the button is positioned so that the lugs engage the raised sections 29 then a relatively small valve opening is given, providing an oxygen flow suitable for administration to infants. When the lugs may enter the spaces between the sections 29 a greater valve opening is achieved, with flow suitable for adults.

When the pressure at the patient reaches a predetermined level the force generated at diaphragm 16 is sufficient to overcome the load applied by spring 22 and the diaphragm 16 will return to its rest position thus preventing the further flow of gas to the patient. This predetermined pressure is lower when the button 25 is set for infant resuscitation because the compression of spring 22 is less.

The characteristics of the diaphragm 35 are so selected as to have substantially the same resistance to opening and volume flow characteristics as the valve 11 over the centre band of the range of flow rate so giving a particular air/oxygen ratio. Use of the backward-facing step resulting in the air flow entraining oxygen means that this particular ratio can also be substantially maintained at the extreme limits of the range of flow rates. The cross-sectional area of the oxygen passages 37 is chosen with a view to achieving this constant ratio, and also having regard to the maximum area of air intake through port 38 and selected orifices 41a. Within the desired overall dimensional limitation of the system the maximum air intake area is limited, and the oxygen passage area must therefore also be limited. It is a matter of ordinary skill in the art to select valve characteristics and cross-sectional areas that will give the desired result.

To give greater versatility to the apparatus an additional gas passage linking the annular groove 30 with the groove 36 may be provided, which additional passage may be opened and closed by a control means, for example a simple lever mechanism actuated by the resilient band 39 at predetermined points in its rotation about the chamber.

As previously stated the complete valve is assembled from four modules, although the no-rebreathing module 3 can be omitted for certain uses. This modular construction allows the valve to be dismantled easily for disinfection or sterilisation. The modules are desirably made generally of plastics materials to give a lightweight construction.

While I have herein shown and described the preferred embodiment of this invention have suggested variations therein, other changes and variations may be made therein within the scope of the appended claims without departing from the spirit and scope of this invention.

What I claim is:

1. A device for providing a gas-air mixture or a pure gas supply to a patient, the device comprising a housing including a first chamber defining a breathing gas passage a second chamber defining an air passage and, downstream of both said first and second chambers, a third chamber defining a breathing gas air passage, from which the patient's breathing supply is taken; demand valve means responsive to patient inhalation for admitting gas into said first chamber; air inlet means for admitting air to said second chamber; a non-return valve means for allowing air to flow from said second to said third chamber said second chamber including an outlet opening downstream of said air inlet means and of which the periphery thereof defines a valve seat surface, said non-return valve means comprising a flexible valve means mounted over said outlet opening and being engageable with said seat surface, said seating surface forming part of an upstream wall of said third chamber; at least one passage means from said first to said third chamber by passing said second chamber, said passage means comprising an orifice opening into said third chamber directly adjacent and upstream of said valve seat surface and spaced from said valve seat surface by a backward-facing step, whereby when suction is applied by the patient, air is drawn through said non-return valve from said second chamber to said third chamber thereby creating an aspiration effect at said backward-facing step actuating said demand valve means and causing breathing gas to flow through said passage to provide a gas-air mixture in said third chamber and means for over-riding said demand valve means to allow a constant flow of gas into said first chamber and through said passage means into said third chamber with said non-return valve means held closed.

2. A device as claimed in claim 1 wherein said opening is of annular form and the flexible valve is a diaphragm covering said opening.

3. A device as claimed in claim 2 wherein an annular groove is formed in said seating surface concentric with and circumferentially surrounding said diaphragm, and said orifice opens into the base of said annular groove.

4. A device as claimed in claim 1 and including means for controlling the volume of air admitted into said second chamber.

5. A device as in claim 1 wherein the opening characteristics of said demand valve and said non-return valve and the total cross-sectional area of said orifice being such that the resistance to flow of air and gas are substantially equal.

* * * * *